(12) United States Patent
Nystrom

(10) Patent No.: US 9,427,515 B1
(45) Date of Patent: Aug. 30, 2016

(54) MONITORING LOW PRESSURES IN HIGH PRESSURE ENVIRONMENTS

(71) Applicant: ACIST MEDICAL SYSTEMS, INC., Eden Prairie, MN (US)

(72) Inventor: Sidney Donald Nystrom, Shoreview, MN (US)

(73) Assignee: ACIST MEDICAL SYSTEMS, INC., Eden Prairie, MN (US)

( * ) Notice: Subject to any disclaimer, the term of this patent is extended or adjusted under 35 U.S.C. 154(b) by 662 days.

(21) Appl. No.: 13/800,969

(22) Filed: Mar. 13, 2013

Related U.S. Application Data

(60) Provisional application No. 61/754,324, filed on Jan. 18, 2013.

(51) Int. Cl.
*A61B 5/02* (2006.01)
*A61M 5/00* (2006.01)

(52) U.S. Cl.
CPC .................................... *A61M 5/007* (2013.01)

(58) Field of Classification Search
None
See application file for complete search history.

(56) References Cited

U.S. PATENT DOCUMENTS

| | | | |
|---|---|---|---|
| 4,226,124 A * | 10/1980 | Kersten | A61B 5/021 128/DIG. 13 |
| 4,375,182 A | 3/1983 | Zavoda | |
| 5,335,584 A | 8/1994 | Baird | |
| 5,449,003 A | 9/1995 | Sugimura et al. | |
| 7,094,216 B2 | 8/2006 | Trombley, III et al. | |
| 7,373,826 B2 | 5/2008 | Weber et al. | |
| 7,389,788 B2 | 6/2008 | Wilson et al. | |
| 7,610,936 B2 | 11/2009 | Spohn et al. | |
| 2003/0122095 A1 * | 7/2003 | Wilson | A61B 5/0215 251/12 |
| 2006/0180202 A1 * | 8/2006 | Wilson | A61B 5/0215 137/112 |
| 2008/0058720 A1 * | 3/2008 | Spohn | A61M 5/007 604/140 |
| 2008/0154214 A1 | 6/2008 | Spohn et al. | |

OTHER PUBLICATIONS

LogiCal® the innovative pressure transducer system; Smiths Medical International Ltd., 2006, 2 pages, Kent, United Kingdom.
U.S. Appl. No. 13/586,658, filed Aug. 15, 2012, Monitoring Blood Pressure in a Medical Injection System, 37 pages.

* cited by examiner

*Primary Examiner* — Etsub Berhanu
(74) *Attorney, Agent, or Firm* — Fredrikson & Byron, P.A.

(57) ABSTRACT

A relatively compact protective apparatus for a pressure sensor includes a diaphragm, a plate, and a sleeve that couples the sensor to the apparatus; the diaphragm, whose perimeter edge is attached to the sleeve between the plate and sleeve, forms a compressible cavity in fluid communication, via an opening in the plate, with another cavity formed between the plate and the coupled sensor. A diameter of the diaphragm is relatively small, so the diaphragm includes an undulating zone for enhanced sensitivity in response to pressure. A configuration of the cavities and the opening allows a contained volume of air to transmit a relatively low pressure, via the diaphragm, to the coupled pressure sensor, yet prevents transmission of relatively high pressures to the pressure sensor. A wall of a system fluid circuit line or a manifold connector may be configured to incorporate the protective apparatus therein.

39 Claims, 10 Drawing Sheets

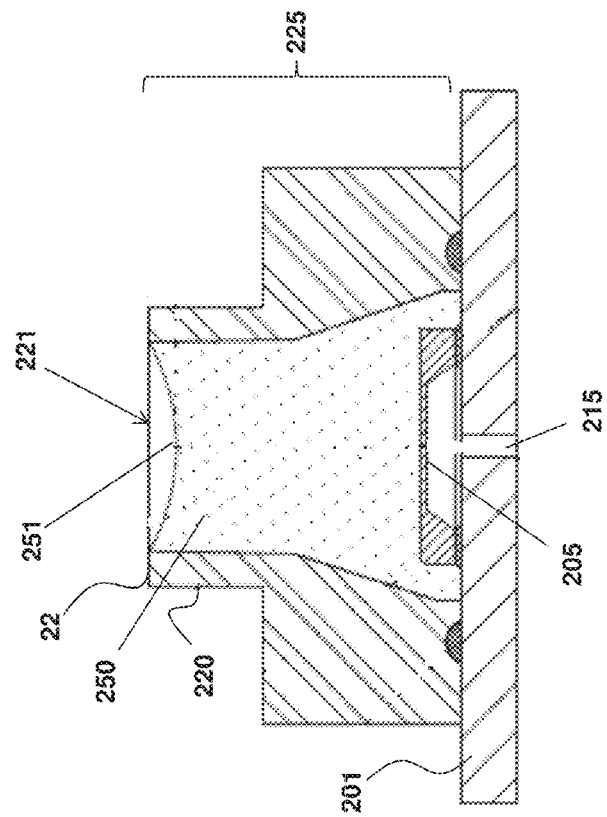
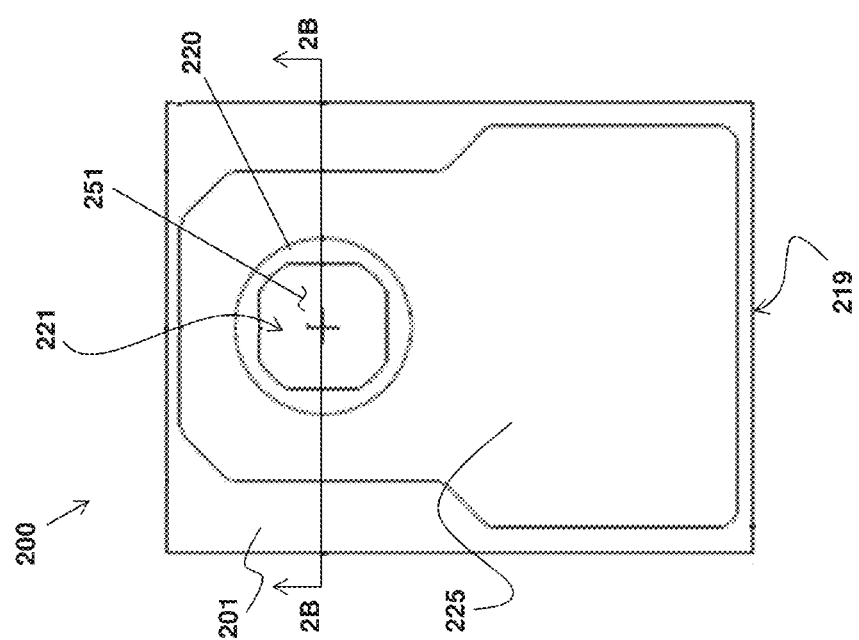
FIGURE 2B
FIGURE 2A

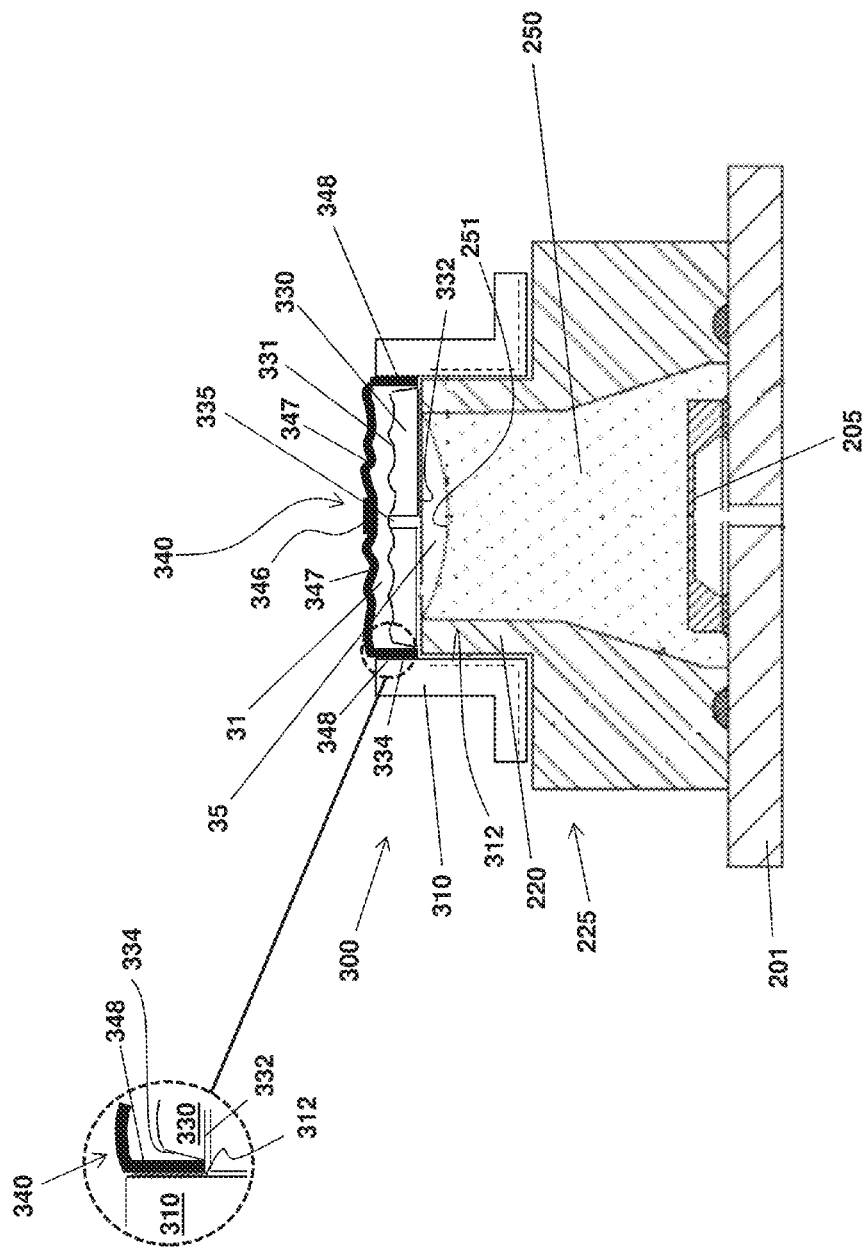

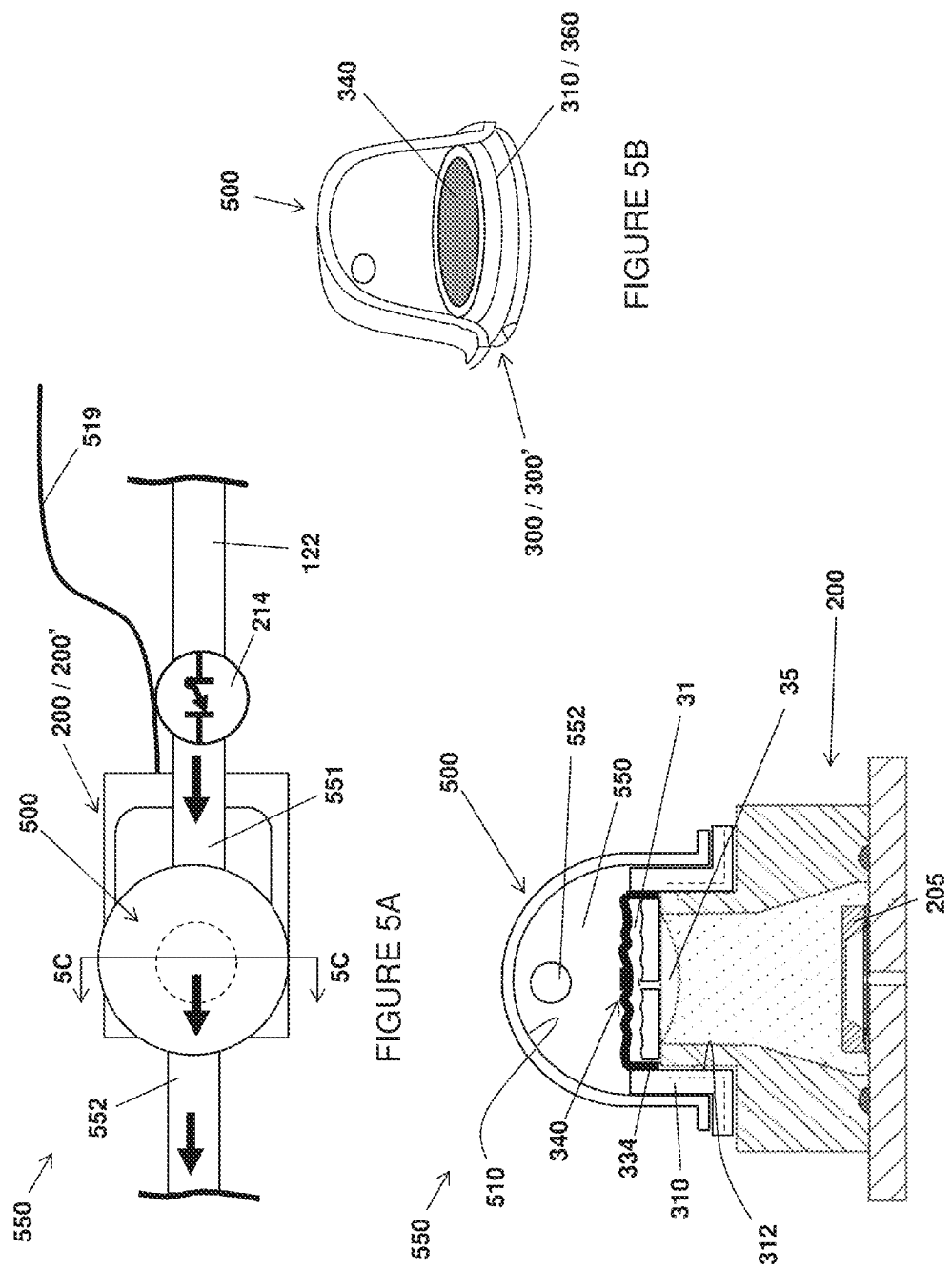

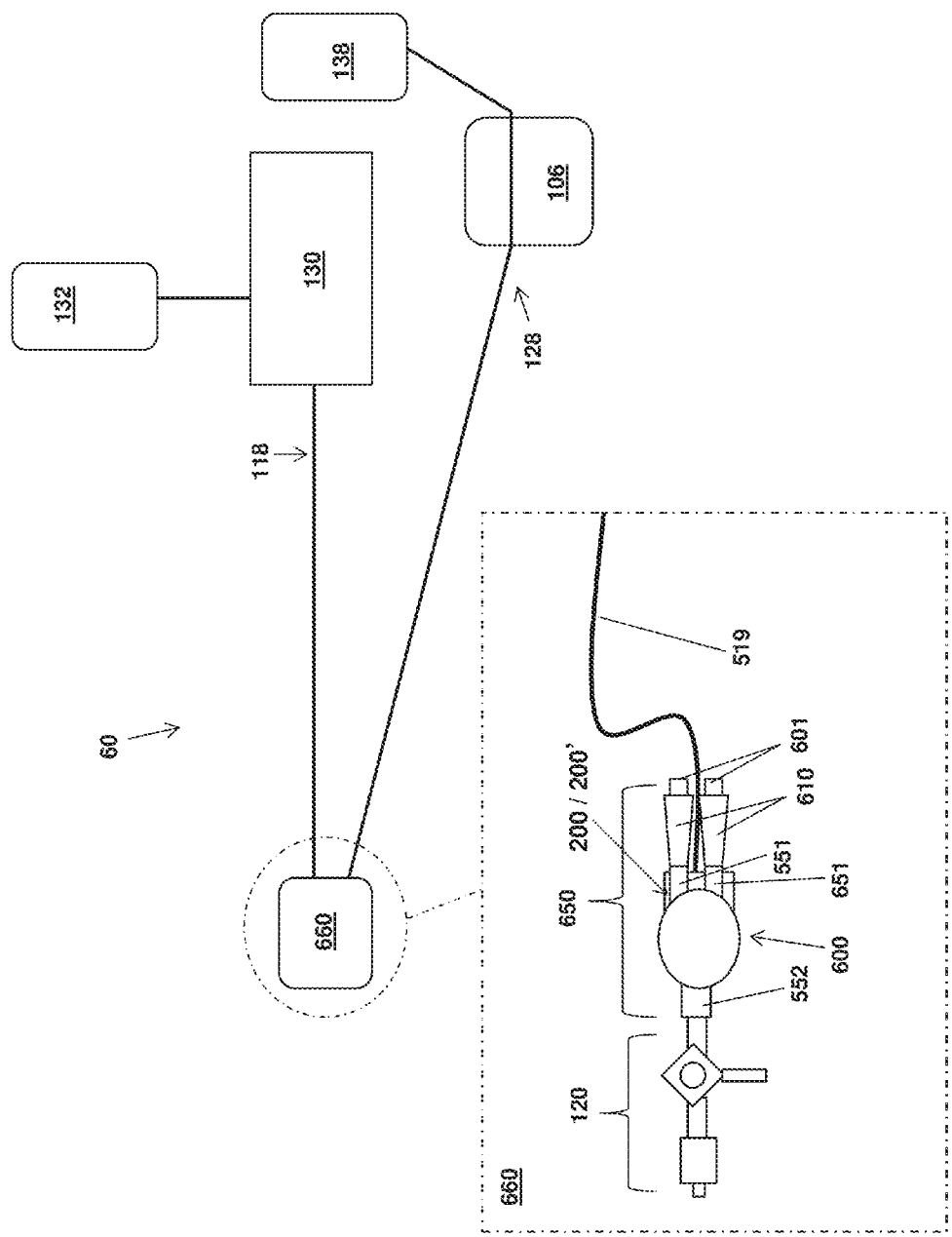

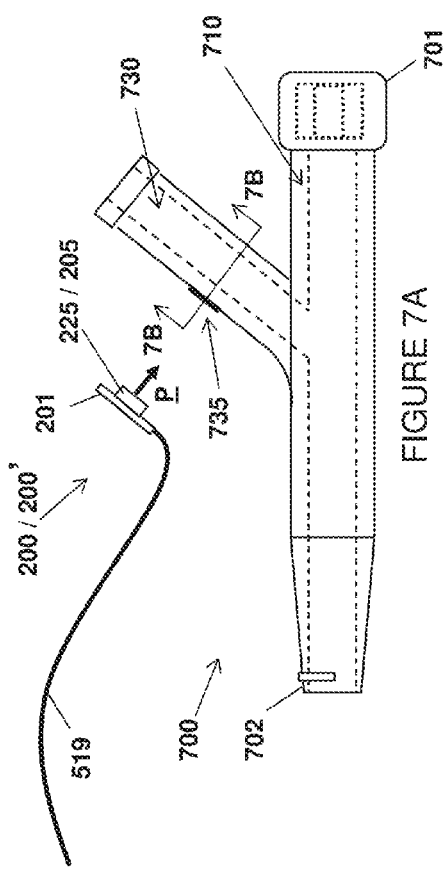
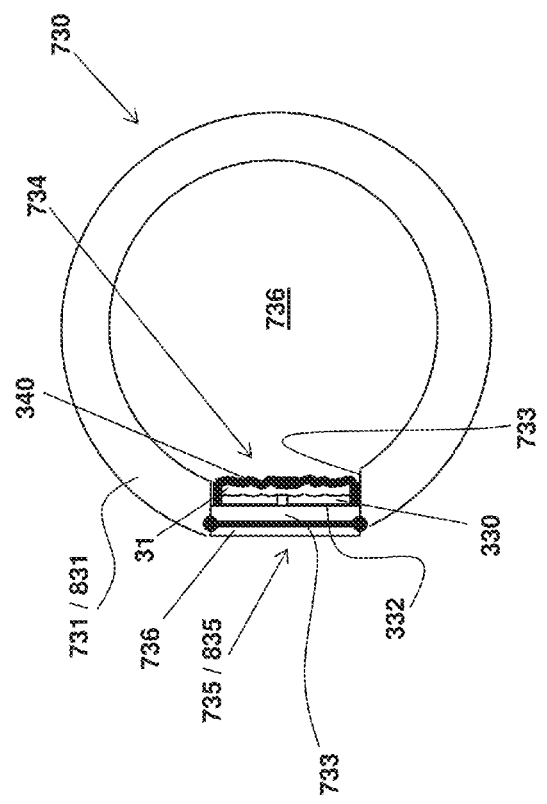

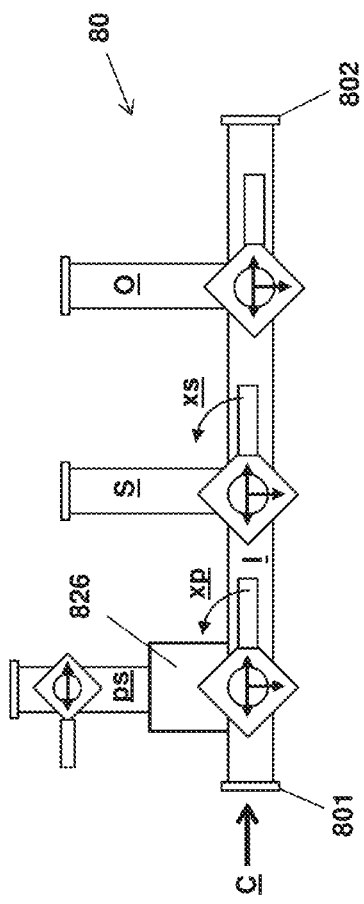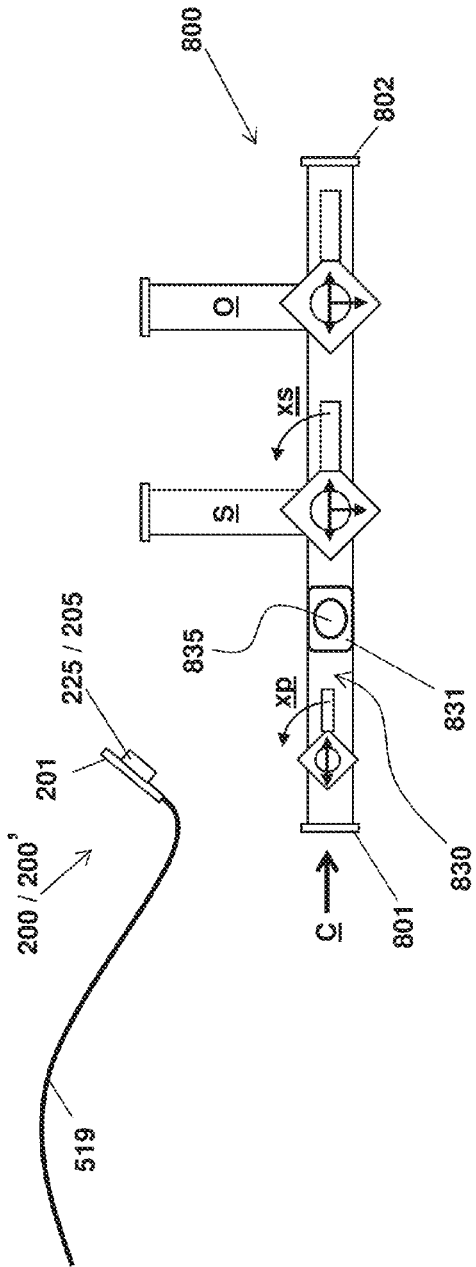
FIGURE 8A
FIGURE 8B

MONITORING LOW PRESSURES IN HIGH PRESSURE ENVIRONMENTS

TECHNICAL FIELD

The present disclosure pertains to pressure monitoring and more particularly to means for integrating relatively low pressure-monitoring sensors into systems having relatively high pressure environments.

BACKGROUND

A medical injection system, for example, to deliver a contrast agent into a patient's vascular system for medical imaging, typically includes a pressure sensor integrated into a fluid circuit of the system for the purpose of monitoring the patient's blood pressure during the imaging procedure. Because contrast media is injected at pressures that are significantly higher (e.g., up to 1200 psi) than the blood pressure being monitored (e.g., between 0 and 5 psi), the typical blood pressure-monitoring pressure sensor is protected from exposure to the high injection pressures, for example, by isolating that portion of the fluid circuit to which the pressure sensor is coupled from that portion through which the high pressure injection flows. One example of such a medical injection system, the ACIST $CV_i$™ system, is shown in FIG. 1.

FIG. 1 is a perspective view of an exemplary medical injection system 100 wherein a first fluid reservoir 132 supplies a pressurizing unit 130 for injection of, for example, a radiopaque contrast agent, into a patient's vascular system via a fluid circuit line 118 that feeds into a patient fluid circuit line 122. FIG. 1 further illustrates a second fluid reservoir 138 from which a diluent, such as saline, is drawn by a peristaltic pump 106 through yet another fluid circuit line 128 that feeds into line 122. The fluid circuit of system 100 further includes a manifold valve 124 and associated sensor 114 to control the flow of fluids into line 122, from pressurizing unit 130, via line 118, and from line 128. When valve 124 is open to line 128 and closed to line 118, and line 122 is coupled to the patient's vascular system, for example, by a catheter connected to line 122 at a connector 120, a pressure transducer assembly 126, which is integrated into line 128, monitors the patient's blood pressure. But, when pressurizing unit 130 is activated to inject a contrast agent, valve 124 is switched to allow the relatively high pressure flow from pressurizing unit 130 into line 122, and to isolate line 128 from the high pressure flow, not only to prevent backflow into line 128, but to also protect the pressure transducer of assembly 126 from exposure to the relatively high injection pressures that could damage the pressure sensor thereof.

One example of a pressure transducer assembly that may be employed by system 100 is the LogiCal® system available from Smiths Medical International; and another example is the Meritrans® available from Merit Medical Systems, Inc. Each of the aforementioned transducer assemblies includes a relatively low cost and disposable pressure sensor (e.g., intended for use in a single medical procedure), with an operating range that is suitable for blood pressure measurements. Thus, as alluded to above, this type of sensor would be rendered inoperable for blood pressure monitoring in between multiple injections (common in a single medical imaging procedure), if exposed to the relatively high injection pressures. Although more robust pressure sensors, which are sensitive enough for blood pressure monitoring, yet are not damaged by exposure to the higher injection pressures, are available, the cost of such sensors is prohibitive for disposable/single use medical applications. Co-pending and commonly assigned U.S. patent application Ser. No. 13/586,658 (filed on Aug. 15, 2012), which is hereby incorporated by reference, discloses apparatus and methods for isolating disposable blood pressure-monitoring pressure sensors from relatively high injection pressures in a medical injection system. Yet, there is still a need for more improved means of integrating relatively low cost and low pressure-monitoring sensors into relatively high pressure environments, while providing protection against damage from the relatively high pressures.

SUMMARY

Embodiments of the present invention are directed toward isolating, or protecting a disposable/single use, or relatively inexpensive, type of low pressure-monitoring sensor, from relatively high pressures, for example, injection pressures in a medical injection system. According to some embodiments, a protective apparatus includes a sleeve that fits around such a pressure sensor, to couple the sensor to the apparatus in a relatively compact package. The apparatus further includes a plate, which has an opening formed therethrough, and a flexible gas-permeable diaphragm, which extends over the plate to form a compressible cavity with the plate; a perimeter edge of the diaphragm is attached to the sleeve between an outer perimeter surface of the plate and the sleeve. Another cavity is formed between the plate and the coupled pressure sensor, and is in fluid communication with the compressible cavity, via the opening. According to preferred embodiments, a maximum diameter of the plate, which approximately corresponds to that of the pressure sensor, is relatively small (e.g., between approximately 2.5 mm an approximately 3 mm), and the diameter of the flexible diaphragm is likewise relatively small; thus, the diaphragm is formed (e.g., from a rubber material) with an undulating zone for stress reduction and enhanced sensitivity in response to pressure. A volume of air, or other suitable compressible fluid, which is contained in the cavities and the opening of the plate, is preferably no greater than approximately six cubic millimeters; and a configuration of the cavities and opening allows the volume to transmit a patient's blood pressure to the coupled pressure sensor, via the diaphragm, when the diaphragm is exposed to flow through a fluid channel of the system, yet prevents the volume from transmitting the relatively high, and potentially damaging, pressures of injection flow to the pressure sensor.

According to some embodiments, the undulating zone of the diaphragm is a peripheral zone that extends between a central zone, which is aligned over the opening in the plate, and the aforementioned perimeter edge, which is attached to the sleeve; the peripheral zone preferably includes a series of annular corrugations and a series of spoke-like corrugations, wherein each spoke-like corrugation radiates from the central zone to the perimeter edge and intersects each annular corrugation.

A fluid circuit line or manifold connector, for example, for use in a medical injection system, according to some embodiments, incorporates the above-described protective apparatus within a wall thereof, wherein the pressure sensor may be permanently coupled to the protective apparatus, or temporarily coupled for replacement thereof. According to some alternate embodiments, the protective apparatus and pressure sensor are coupled to a flow chamber, which is formed by a cap coupled to the sleeve of the protective apparatus, wherein the cap includes at least one inlet port and an outlet port, and defines a flow chamber over the diaphragm, on an opposite side thereof from the compressible cavity.

It should be noted that embodiments of the present invention will find application in other areas, besides medical injection systems, where it is desirable to employ relatively low cost, mass-produced pressure sensors for measuring/monitoring relatively low pressures without concern for exposure to relatively high pressures outside the range of the sensors. Examples of other potential medical applications include, without limitation, pressure monitoring for wound therapy machines, for hospital beds, and for oxygen concentrators, or even for other types of medical infusion devices, for example, hand manifolds.

BRIEF DESCRIPTION OF THE DRAWINGS

The following drawings are illustrative of particular methods and embodiments of the present disclosure and, therefore, do not limit the scope of the invention. The drawings are not to scale (unless so stated) and are intended for use in conjunction with the explanations in the following detailed description. Methods and embodiments will hereinafter be described in conjunction with the appended drawings, wherein like numerals denote like elements, and:

FIG. 2A is a plan view of an exemplary sensor subassembly;

FIG. 2B is a cross-section view along section line 2B-2B of FIG. 2A;

FIG. 3A a cross-section view of a protective apparatus assembled together with the pressure sensor of the subassembly shown in FIGS. 2A-B, according to some embodiments;

FIG. 5A is a plan view of a portion of a fluid circuit for a medical injection system, according to some embodiments;

FIG. 5B is perspective view with a partial cross-section of a portion of the fluid circuit of FIG. 5A, according to some embodiments;

FIG. 5C is a cross-section view along section line 5C-5C of FIG. 5A, according to some embodiments;

FIG. 6 is a block diagram of an injection system fluid circuit with an enlarged plan view of a portion thereof, according to some embodiments;

FIG. 7A is a plan view of a manifold connector, according to some embodiments, and a pressure sensor subassembly positioned for coupling thereto;

FIG. 7B is a cross-section view along section line 7B-7B of FIG. 7A, according to some embodiments;

FIG. 8A is a plan view of another type of manifold connector; and

FIG. 8B is a plan view of the other type of manifold connector, which has been modified, according to some embodiments.

DETAILED DESCRIPTION

Figure 1:
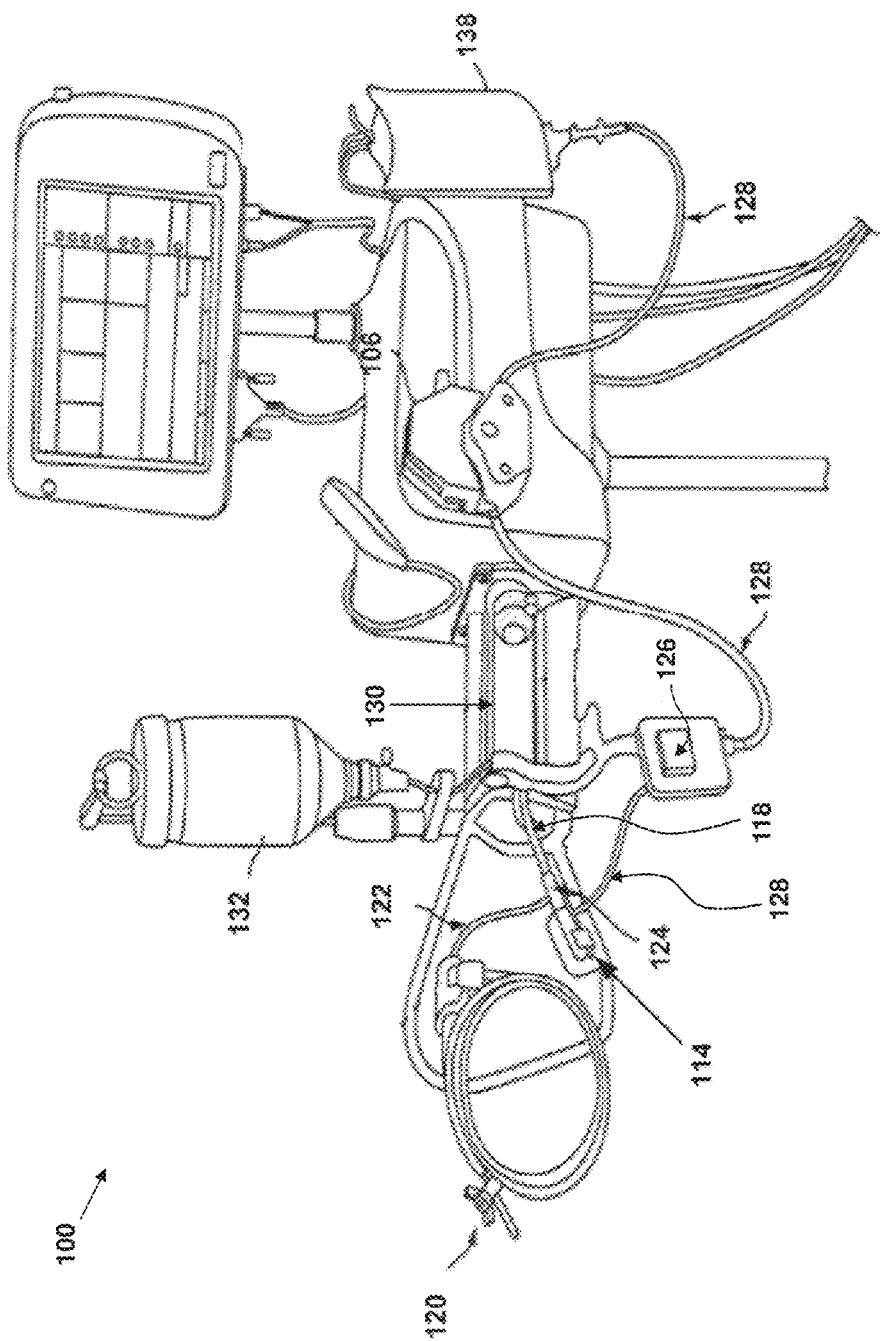
FIG. 1 is a perspective view of an exemplary medical injection system.

The following detailed description is exemplary in nature and is not intended to limit the scope, applicability, or configuration of the invention in any way. Rather, the following description provides practical illustrations for implementing exemplary methods and embodiments. Examples of constructions, materials and dimensions are provided for selected elements, and all other elements employ that which is known to those of skill in the field of the invention. Those skilled in the art will recognize that many of the examples provided have suitable alternatives that can be utilized.

FIG. 2A is a plan view of an exemplary pressure sensor subassembly 200, for example, the Model 1620 solid state pressure transducer available from Measurement Specialties, Inc. FIG. 2A illustrates subassembly 200 including a pressure sensor 225 mounted on a substrate 201, for example, a ceramic substrate. FIG. 2B is a cross-section view along section line 2B-2B of FIG. 2A, and shows pressure sensor 225 including a pressure sensing element 205, for example, a fully piezoresistive silicon pressure sensor, which is exposed to atmospheric pressure via a vent hole 215 through substrate 201, an isolation layer 250, for example, a dielectric gel, which overlays sensing element 205, and a cup 220, which contains sensing element 205 and isolation layer 250 and has an opening 221 through which a recessed surface 251 of isolation layer 250 is exposed. Not shown are thick film resistors formed in substrate 201, for compensation and calibration, and contact pads formed in substrate 201 at the general location designated by reference numeral 219 in FIG. 2A. Sensor subassembly 200 is thus configured for measuring pressure in a fluid channel, when surface 251 of isolation layer 250 is exposed to flow through the channel.

FIG. 3A a cross-section view of a protective apparatus 300 assembled together with pressure sensor 225 of sensor subassembly 200, according to some embodiments of the present invention, wherein an inner perimeter surface 312 of a sleeve 310 of protective apparatus 300 is fitted about a perimeter of isolation layer 250. FIG. 3A illustrates protective apparatus 300 further including a plate 330, which has an opening 335 formed therethrough, and a flexible, gas-permeable diaphragm 340, which extends over a first side 331 of plate 300 to form a compressible cavity 31 therewith. According to the illustrated embodiment, a perimeter edge 348 of diaphragm 340 is attached to sleeve 310, between sleeve 310 and an outer perimeter surface 334 of plate 330, which is preferably tapered, as is best seen in the enlarged detail of FIG. 3A. FIG. 3A further illustrates a second side 332 of plate extending over surface 251 of isolation layer 250 to form another cavity 35, which in fluid communication with compressible cavity 31, via opening 335 in plate 310.

According to the illustrated embodiment, a volume of air, or other suitable compressible fluid, is contained in cavities 31, 35 and in opening 335; and a configuration of cavities 31, 35 and opening 335 allows the contained volume to transmit a relatively low pressure (e.g., between zero and approximately five to ten psi) to the coupled pressure sensor 225, via uninhibited movement of diaphragm 340, when exposed to flow through a fluid circuit, for example, of a medical system (e.g., system 100 of FIG. 1), yet prevents the volume from transmitting relatively high, and potentially damaging, pressures, for example, of injection flow, to pressure sensor 225. The relatively high pressure may be any pressure that is greater than between approximately ten psi and approximately 100 psi, preferably greater than approximately fifty psi, for example, the injection pressures, which can be up to 1200 psi. According to some preferred embodiments, the contained volume is no greater than approximately six cubic millimeters, and a ratio of the portion of the volume contained within compressible cavity 31 to the portion of the volume contained within cavity 35, when apparatus 300 is coupled to pressure sensor 225, is between approximately one and approximately three. This contained volume does not significantly impact compliance of a fluid circuit, to which the assembly of protective apparatus 300 and pressure sensor 225 is coupled, so the frequency response of sensing element 205 when monitoring blood pressure is not degraded. With further reference to FIG. 3A, recessed surface 251 of isolation layer 250 is shown in the form of a meniscus, which according to preferred embodiments, has a maximum depth, relative to second side 332 of plate 330, of no more than approximately 0.035 inch.

With further reference to FIG. 3A, sleeve 310 is shown fitted around cup 220 of pressure sensor 225, for example, for bonding thereto, via an adhesive, for example, a cyanoacrylate adhesive like Loctite® 4541™, or a UV-cure adhesive like Locktite® 3311™, which may be held in an annular channel (shown with dashed lines) that is formed in an inner surface 312 of sleeve 310. According to some methods, the adhesive is applied to inner surface 312, prior to fitting sleeve 310 around cup 220 of pressure sensor 225, and then extruded into the annular channel in the process of fitting sleeve 310 around cup 220. According to some alternate methods, the adhesive is injected into the annular channel of sleeve inner surface 312, after fitting sleeve 310 around cup 220, via one of a pair of weep channels (also shown with dashed lines in FIG. 3A), wherein the other of the pair of weep channels forms a vent to facilitate the wicking (e.g., by capillary action) of the adhesive within the annular channel and around the perimeter of cup 220.

Diaphragm 340, which is preferably formed from silicone rubber, may be insert-molded to sleeve 310, for the attachment of perimeter edge 348 to sleeve 310, according to methods known in the art; and then plate 330 may be press fit within inner perimeter surface 312 of sleeve 310 such that the attached perimeter edge 348 of diaphragm 340 is located between sleeve 310 and outer perimeter surface 334 of plate 330, as shown in FIG. 3A. It may be appreciated that the illustrated and aforementioned taper of outer perimeter surface 334 facilitates such an assembly of plate 330 into sleeve 310. Furthermore, the interface between perimeter edge 348 of diaphragm 340, when formed from silicone rubber, and a maximum diameter portion of outer perimeter surface 334 of plate 330, adjacent side 332, will create a seal therebetween, and provide sufficient holding force to retain plate 330 within sleeve 310 until protective apparatus 300 is assembled around cup 220 of pressure sensor 225, for example, so that side 332 of plate 330 seats against a rim 22 (FIG. 2B) of cup 220. Diaphragm 340 is preferably formed from silicone rubber, not only for its flexibility and manufacturing advantages, but also because silicone rubber is gas-permeable to allow effective EtO sterilization of protective apparatus 300, and to allow sensing element 205 to equilibrate to local atmospheric pressure. According to an exemplary embodiment, 917CK silicone rubber (Minnesota Rubber & Plastics of Minneapolis, Minn.), which is preferably natural/translucent and has a durometer in the range of approximately 40-55, on a Shore A scale, forms diaphragm 340. Sleeve 310 and plate 330 are each preferably formed from a polycarbonate, for example, APEC® 1745, which is known in the art.

According to preferred embodiments of the present invention, the coupling of pressure sensor 225 to protective apparatus 300 results in a relatively compact package, for example, when a diameter of the portion of cup 220, about which sleeve 310 is fitted, is approximately ⅛ of an inch, an outer diameter of sleeve 310 is approximately 3/16 of an inch. Therefore, a corresponding diameter of plate 330 is relatively small, for example, having a diameter of between approximately 0.1 inch (2.5 mm) and approximately 0.12 inch (3 mm), at the maximum diameter portion of outer perimeter surface 334, and a diameter of flexible diaphragm 340 is likewise relatively small. If diaphragm 340 were flat, that is, un-contoured across the active surface thereof, such a relatively small diameter could compromise sensitivity for blood pressure monitoring, since sensitivity is proportional to the diaphragm radius to the $4^{th}$ power. Thus, for enhanced sensitivity, as well as stress reduction, diaphragm 340 is formed (e.g., from the aforementioned silicone rubber material) with a contoured, or undulating zone 347, which allows deflection without significant stress/stretch of diaphragm 340, and which is described below, in conjunction with FIGS. 4A-B.

Figure 3B:
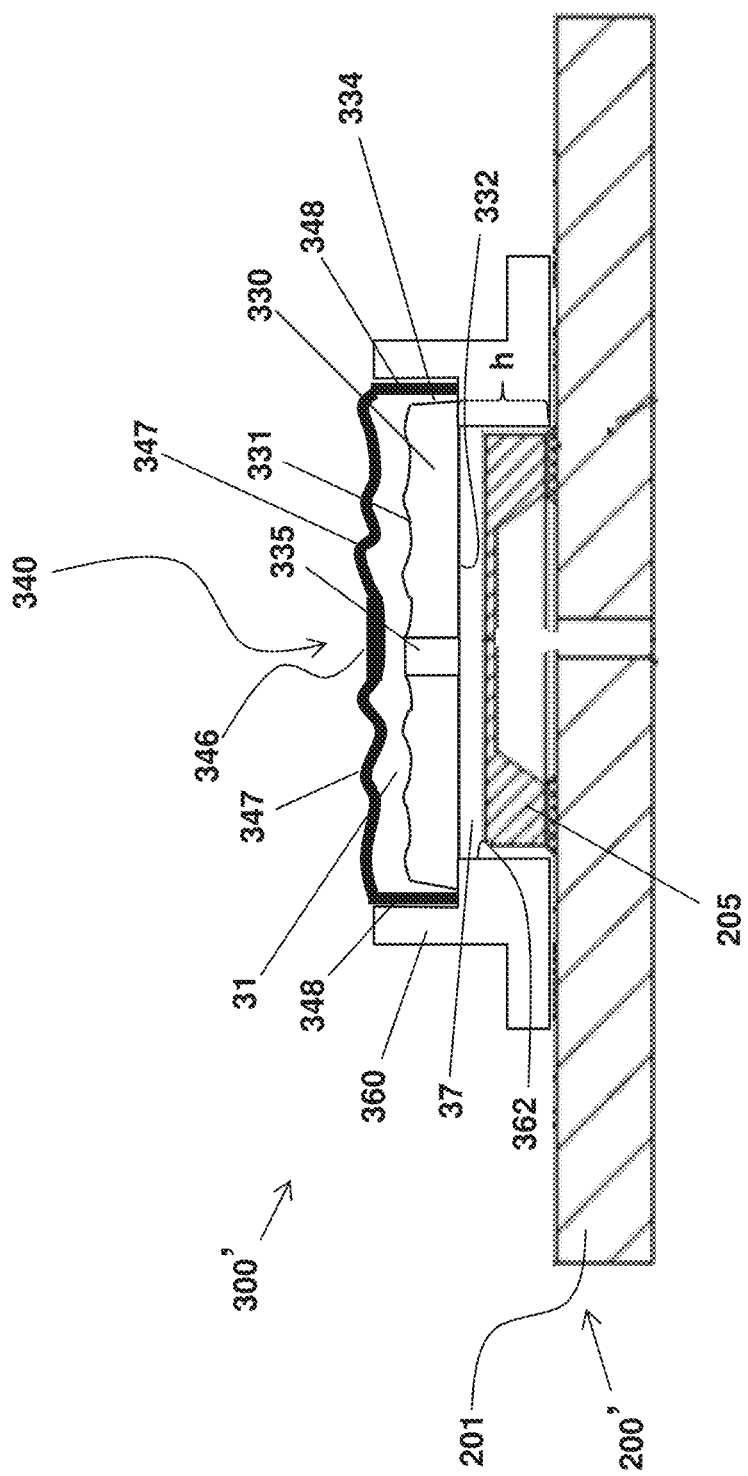
FIG. 3B is a cross-section view of a protective apparatus coupled to a sensor subassembly, according to some alternate embodiments.

FIG. 3B is a cross-section view of a protective apparatus 300' coupled to a sensor subassembly 200', according to some alternate embodiments, wherein pressure sensing element 205 is mounted on substrate 201, like subassembly 200, but no isolation layer or cup are included. Thus, FIG. 3B illustrates an even more compact package than that of FIG. 3A, wherein an interior perimeter surface 362 of a sleeve 360 of apparatus 300' is configured to directly fit around pressure sensing element 205; and, when sleeve 360 is mounted on substrate 201, as shown, a height h of inner perimeter surface 362 supports second side 332 of plate 330 above pressure sensing element 205 so that cavity 37 is formed therebetween. It should be noted that the 'more compact package' of FIG. 3B is suitable for applications in which high voltage electrical isolation, for example, as provided by isolation layer 250 of pressure sensor 225, is not required. Like apparatus 300, apparatus 300' includes diaphragm 340, which extends over first side 331 of plate 330 to form compressible cavity 31, and whose perimeter edge 348 is captured between outer perimeter surface 334 of plate 330 and sleeve 360, which may also be formed from a polycarbonate, for example, APEC® 1745. Furthermore, the contained volume of cavities 31 and 37 and opening 335, like that of apparatus 300 coupled to pressure sensor 225, is no greater than approximately six cubic millimeters, and a ratio of the portion of the volume contained within compressible cavity 31 to the portion of the volume contained within cavity 37 is between approximately one and approximately three.

Figure 4A:
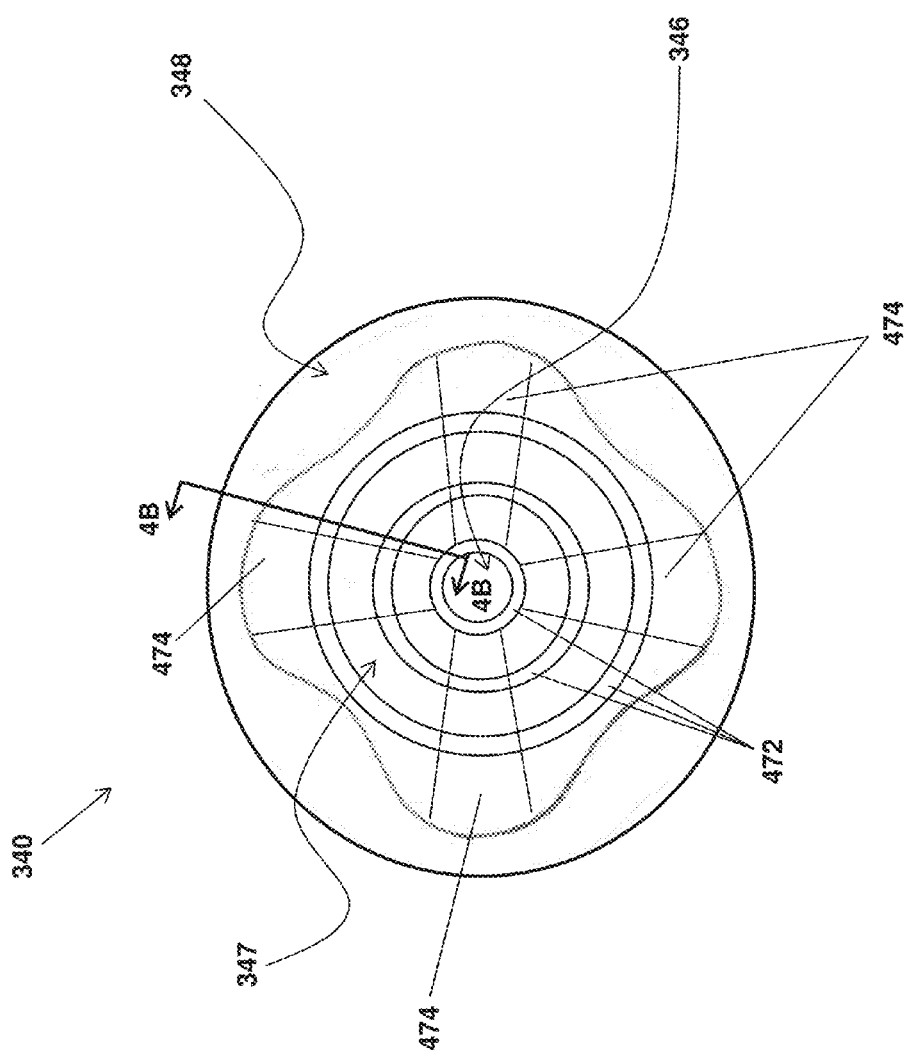
FIG. 4A is a plan view of a flexible diaphragm for a protective apparatus, according to some embodiments.
Figure 4B:
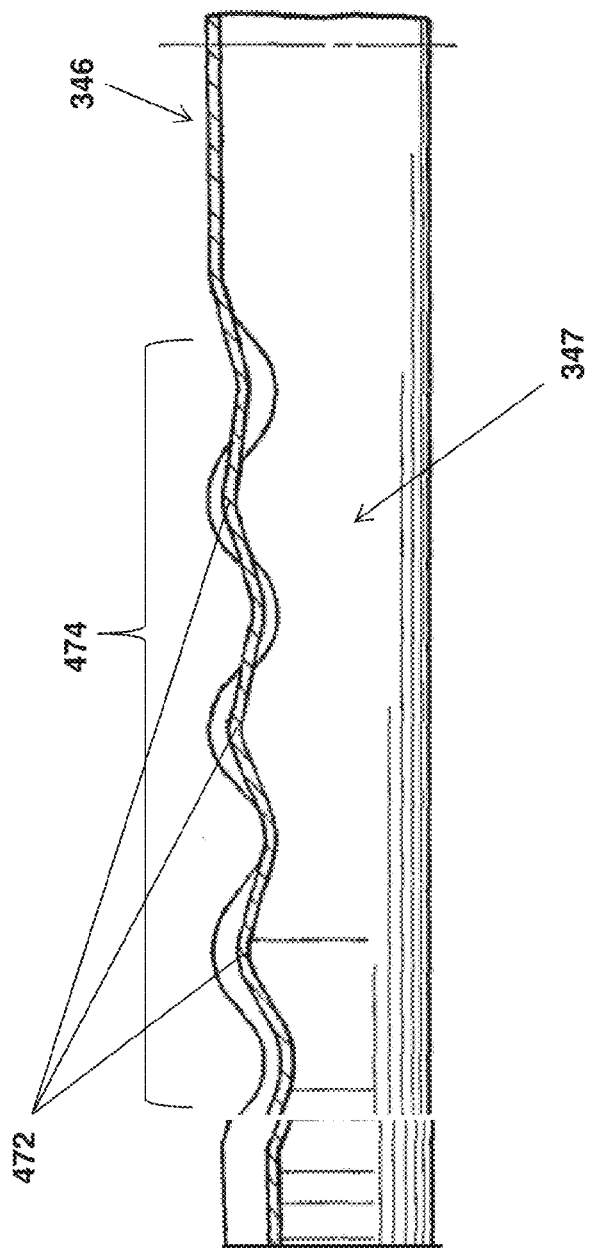
FIG. 4B is a cross-section view along section line 4B-4B of FIG. 4A, according to some embodiments.

FIG. 4A is a plan view of diaphragm 340, according to some embodiments. FIG. 4A illustrates diaphragm 340 including the aforementioned undulating peripheral zone 347 and perimeter edge 348, and a central zone 346, wherein peripheral zone 347 extends between perimeter edge 348 and central zone 346. FIG. 4A further illustrates undulating peripheral zone 347 of diaphragm 340 including a series of annular corrugations 472, and a series of spoke-like corrugations 474, each of which radiates outward from central zone 346 to perimeter edge 348 and intersects each annular corrugation 472. FIG. 4B, which is a cross-section view along section line 4B-4B of FIG. 4A, shows, in relief, annular corrugations 472 and one of spoke-like corrugations 474. A ratio of peak-to-peak amplitude to wavelength for each pair of adjacent annular corrugations 472 is preferably less than 0.5. Each spoke-like corrugation 474 is a half waveform, and has an amplitude that decreases from a maximum, in proximity to perimeter edge 348, to a minimum, in proximity to central zone 346. Similarly, annular corrugations 472 decrease in amplitude from perimeter edge 348 to central zone 346. As mentioned above, according to preferred embodiments of diaphragm 340, the diameter of diaphragm 340 at the intersection of undulating peripheral zone 347 and perimeter edge 348 is between approximately 2.5 mm (0.1 inch) and approximately 3 mm (0.12 inch). Although three annular corrugation 472 and four spoke-like corrugations 474 are illustrated, an increased number of each may be preferred for some alternate embodiments, if manufacturing and material limitations allow. U.S. Pat. No. 4,375,182 discloses similar dual stress-relief structures (e.g., annular and spoke-like corrugations) formed in diaphragms, the teaching of which is hereby incorporated by reference. A nominal thickness of diaphragm 340, over undulating peripheral zone 347, is preferably approximately constant, and, according to an exemplary embodiment, is between approximately 0.01 inch (0.25 mm) and approximately 0.012 inch (0.3 mm).

With reference back to FIGS. 3A-B, central zone 346 of diaphragm 340 is aligned over opening 335 of plate 330, and, in order to prevent significant extrusion of central zone 346 into opening 335, when diaphragm 340 is exposed to the aforementioned relatively high pressures, a stiffness of central zone 346 may be greater than that of peripheral zone 347. According to some preferred embodiments, diaphragm 340 is molded such that central zone 346 is formed by a mold gate vestige, and a resulting nominal thickness of central zone 346 is greater than a diameter of opening 335 of plate 330, which is preferably approximately 0.01 inch (0.25 mm). Furthermore, first side 331 of plate 330 may have an undulating contour formed therein, which is generally aligned with, and simulates the series of annular corrugations 472 of diaphragm 340, for example, to minimize a volume of compressible cavity 31 and prevent contact between first side 331 and diaphragm 340, when diaphragm 340 is exposed to the relatively low blood pressures (e.g., from zero to approximately 300 mm Hg). It should be noted that diaphragm 340, when exposed to the aforementioned relatively high pressures, collapses into contact with first side 331 of plate 330, thereby protecting pressure sensing element 205 from the relatively high pressures; and, when the pressure subsides, diaphragm 340 rebounds away from side 331, to again become operable for the transmission of patient blood pressures.

FIG. 5A is a plan view of a portion of a fluid circuit for a medical injection system, for example, like system 100 of FIG. 1, according to some embodiments; and FIGS. 5B-C are corresponding cross-section views. FIG. 5A illustrates an assembly 550 of a cap 500, protective apparatus 300/300' (seen in FIGS. 5B-C), and sensor subassembly 200/200', which is coupled to patient fluid circuit line 122, for example, as a replacement for pressure transducer assembly 126 of system 100. A conductive lead wire 519 is shown coupled to the aforementioned contact pads formed in substrate 201 of sensor subassembly 200/200' (designated by reference numeral 219 in FIG. 2A). With reference to FIG. 1, assembly 550 is integrated into the fluid circuit of system 100 downstream of manifold valve 124, preferably along a distal portion of patient line 122 in close proximity to connector 120, to which a catheter providing access to the patient's vascular system is coupled, so that sensing element 205 may operate in relatively close proximity to the patient to monitor the patient's blood pressure. Monitoring blood pressure in relatively close proximity to the patient is desirable in order to minimize blood pressure signal distortions, which may be caused by mechanical factors imposed by an increased volume of fluid within fluid circuit lines that extend between the patient's vascular system and a pressure sensor. Some of these factors include: 1) fluid resistance due to friction; 2) compliance or stiffness of fluid-filled tubing lines; and 3) fluid inertance (e.g., a measure of pressure gradient in the fluid required to cause a change in flow rate with time).

FIGS. 5A-C further illustrate cap 500 including an inner surface 510 that defines a flow chamber 550, which is located on an opposite side of diaphragm 340 from compressible cavity 31 of protective apparatus 300/300', an inlet port 551, for conducting flow into flow chamber 550, and an outlet port 552 for conducting flow out from flow chamber 550. Connector 120 may be coupled directly to outlet port 552 of cap 500. FIG. 5A further illustrates a check valve 214 located upstream side of inlet port 551, to prevent backflow during blood pressure monitoring. According to the illustrated embodiment, cap 500 extends around an outer perimeter surface of sleeve 310/360 and may be bonded thereto, for example, by ultrasonic welding. Cap 500, like sleeve 310/360, may be formed by injection molding, from a relatively rigid plastic, preferably the aforementioned preferred polycarbonate (APEC® 1745).

FIG. 6 is a block diagram of an injection system fluid circuit 60 with an enlarged plan view of a portion 660 thereof, according to some embodiments. FIG. 6 illustrates portion 660 including the aforementioned connector 120 and an assembly 650 connected thereto, which may be packaged as a disposable kit. Assembly 650 is similar to assembly 550 of FIGS. 5A-C, in that assembly 650 includes protective apparatus 300/300' coupled to sensor subassembly 200/200' (not shown), but a cap 600 of assembly 650 includes two inlet ports 551 and 651 that may be connected to lines 118 and 128, respectively, of fluid circuit 60 via corresponding connectors 601, so that patient fluid line 122 is not necessary. Fluid circuit 60, like that of system 100 of FIG. 1, is shown including first fluid reservoir 132 that supplies pressurizing unit 130 for injection of radiopaque contrast agent, into a patient's vascular system via fluid circuit line 118, and second fluid reservoir 138 from which saline is drawn by peristaltic pump 106 through fluid circuit line 128 for injection. FIG. 6 further illustrates a check valve 610 coupled between each of inlet ports 551, 651 and the corresponding connector 601 to prevent backflow into lines 118, 128 during physiologic pressure monitoring. Since saline may be directly flushed through the flow chamber in cap 600 (similar to that in cap 500), at port 651, after a contrast injection through port 551, the fluid between the patient's vascular system and sensor subassembly 200/200' may have a lower viscosity (less residual contrast and more saline), resulting in greater signal fidelity for improved pressure monitoring.

FIG. 7A is a plan view of a manifold connector 700, according to some embodiments, wherein sensor subassembly 200/200' is shown positioned for coupling pressure sensor/sensing element 225/205 thereof within an aperture 735 thereof; and FIG. 7B is a cross-section view along section line 7B-7B of FIG. 7A, according to some embodiments. FIG. 7A illustrates manifold connector 700 including an injection channel 730, which is configured for connection to an injection line of a medical injection system, for example, patient fluid line 122 of system 100 (FIG. 1), and an auxiliary channel 710 in fluid communication with injection channel 730. FIG. 7A further illustrates auxiliary channel 710 extending from a proximal end 701 thereof to a distal end 702 thereof, wherein proximal end 701 is configured with an adjustable sealing member (shown with dotted lines) formed therein (e.g., a Tuohy-Borst type seal known in the art), and distal end 702 is configured for connection to a delivery catheter. (Lumens of the channels of manifold connector 700 are shown with dashed lines in FIG. 7A). Those skilled in the art will appreciate that auxiliary channel 710 may be used for device insertion, wherein an elongate medical device inserted through proximal end 701 of channel 710 is advanced into a patient's vasculature through the aforementioned delivery catheter connected to distal end 702 of channel 710. FIG. 7B illustrates aperture 735 formed in a wall 731 of injection channel 730, and a lumen 736 of injection channel 730 formed by wall 731.

According to the illustrated embodiment, aperture 735 has a perimeter surface 733 that is configured to retain a blood pressure-monitoring pressure sensor, for example, the above-described pressure sensor 225 of sensor assembly 200, or just sensing element 205 of sensor assembly 200'; and FIG. 7B further illustrates a protective apparatus 734 mounted in aperture 735 to protect the retained pressure sensor against the aforementioned relatively high pressures of injection flow (e.g., up to approximately 1200 psi) through lumen 736. According to FIG. 7B, protective apparatus 734, like apparatus 300 and 300' described above, includes plate 330 and flexible diaphragm 340, wherein perimeter edge 348 of diaphragm 340 is attached to perimeter surface 733 of aperture 735, between plate 330 and perimeter surface 733, such that one side of diaphragm 340 is exposed to flow in lumen 736, and the opposite side of diaphragm 340 forms compressible cavity 31 with plate 330. FIG. 7B further illustrates perimeter surface 733 of aperture 735, in proximity to an exterior of wall 731 of injection channel 730, including a seal member 736 fitted therein for a sealing press fit around pressure sensor/sensing element 225/205, such that when retained in aperture 735, plate 330 defines cavity 35 or 37 therewith, as described above. According to some alternate embodiments, a pressure sensor subassembly, for example, like sensor subassembly 200/200', may be more permanently integrated with protective apparatus 734 in wall 731 of injection port 730. With reference back to FIG. 7A, it may be appreciated that, by locating aperture 735 in wall 731 of injection channel 730, which is offset from auxiliary channel 710, protective apparatus 734 is protected from being impinged upon by the aforementioned elongate medical device when inserted through channel 710 from proximal end 701.

FIG. 8A is a plan view of another type of manifold connector 80, which is known in the art, and which includes at least three auxiliary channels, for example, a pressure sensor channel ps, a saline channel S, and another channel O, each of which is in fluid communication, subject to regulation by a corresponding stop cock valve, with a main, injection channel I. FIG. 8A illustrates injection channel I extending between a proximal end 801 thereof and a distal end 802 thereof, wherein proximal end 801 is configured for connection to a fluid line, for example, a contrast agent injection line of a medical injection system, and distal end 802 is configured for connection to a delivery catheter. FIG. 8A further illustrates a pressure transducer assembly 826 (e.g., the aforementioned LogiCal® system available from Smiths Medical International, or the Meritrans® available from Merit Medical Systems, Inc.) integrated into pressure sensor channel ps so as to be isolated from relatively high pressure flow, per arrow C, within injection channel I, when the corresponding stop cock valve is in the illustrated position. According to FIG. 8A, when the stop cock valves that correspond to channels ps and S are rotated per arrows xp and xs, respectively, flow per arrow C is blocked, flow from saline channel S is allowed into injection channel I, and pressure sensor 826 is in fluid communication with injection channel I for blood pressure monitoring via the catheter connected to distal end 802 and extending into a patient's vasculature.

FIG. 8B is a plan view of a manifold connector 800, according to some embodiments, which of the same type as manifold connector 80 of FIG. 8A, but modified by elimination of channel ps. FIG. 8B illustrates an injection channel 830 of manifold connector 800 including an aperture 835 formed in a wall 831 thereof. With reference back to FIG. 7B, aperture 835 of manifold connector 800 is configured as described above, with protective apparatus 734 mounted therein, such that pressure sensor 225 of sensor assembly 200, or just sensing element 205 of sensor assembly 200' can be retained therein for blood pressure monitoring (when the stop cock valve in proximity to proximal end 801 is rotated per arrow xp) and protected by protective apparatus 734 during relatively high pressure injections of contrast agent through channel 830, for example, per arrow C.

In the foregoing detailed description, the invention has been described with reference to specific embodiments. However, it may be appreciated that various modifications and changes can be made without departing from the scope of the invention as set forth in the appended claims. Furthermore, embodiments of the present invention may find application in other areas, besides medical injection systems, where it is desirable to employ relatively low cost, mass-produced pressure sensors for measuring/monitoring relatively low pressures without concern for exposure to relatively high pressures outside the range of the sensors.

I claim:

1. A protective apparatus configured for coupling to a pressure sensor for use in a medical injection system to monitor patient blood pressure, the apparatus comprising:
   a plate including a first side, a second side, opposite the first side, and an opening extending from the first side to the second, the second side of the plate defining a cavity with the pressure sensor when the apparatus is coupled to the pressure sensor;
   a sleeve extending around an outer perimeter surface of the plate and having an inner perimeter surface extending away from the second side of the plate, the inner perimeter surface being sized to fit around a perimeter of the pressure sensor when the apparatus is coupled thereto; and
   a flexible diaphragm extending over the first side of the plate and defining a compressible cavity with the plate, the compressible cavity being in fluid communication with the cavity formed between the second side of the plate and the coupled pressure sensor, via the opening of the plate, the diaphragm being formed from a rubber material, and the diaphragm including a central zone, an undulating peripheral zone, and a perimeter edge, the perimeter edge being attached to the sleeve between the sleeve and the outer perimeter surface of the plate, and the peripheral zone including a series of annular corrugations and a series of spoke-like corrugations, each spoke-like corrugation radiating from the central zone to the perimeter edge and intersecting each annular corrugation.

2. The apparatus of claim 1, wherein the first side of the plate has an undulating contour formed therein, the undulating contour generally aligned with, and simulating the series of annular corrugations of the undulating peripheral zone of the diaphragm.

3. The apparatus of claim 1, wherein a compressible fluid volume contained within the cavities and the opening of the plate, when the apparatus is coupled to the pressure sensor, is no greater than approximately six cubic millimeters.

4. The apparatus of claim 1, wherein a ratio of a compressible fluid volume contained within the compressible cavity, on the first side of the plate, to a compressible fluid volume contained within the cavity, on the second side of the plate, when the apparatus is coupled to the pressure sensor, is between approximately one and approximately three.

5. The apparatus of claim 1, wherein a maximum diameter of the plate, defined at the outer perimeter surface thereof, is between approximately 2.5 mm (0.1 inch) and approximately 3 mm (0.12 inch).

6. The apparatus of claim 1, wherein the outer perimeter surface of the plate is tapered such that a maximum diameter of the plate is located on the second side of the plate.

7. The apparatus of claim 1, wherein a diameter of the opening of the plate is approximately 0.25 mm (0.01 inch).

8. The apparatus of claim 1, wherein a nominal thickness of the central zone of the diaphragm is greater than a diameter of the opening of the plate.

9. The apparatus of claim 1, wherein the central zone of the diaphragm has a stiffness greater than that of the peripheral zone of the diaphragm, the central zone being aligned over the opening of the plate.

10. The apparatus of claim 1, wherein the diaphragm is formed by injection molding, and the central zone of the diaphragm comprises a mold gate vestige.

11. The apparatus of claim 1, wherein a nominal thickness of the undulating peripheral zone of the diaphragm is between approximately 0.01 inch and 0.012 inch.

12. A disposable flow circuit assembly for a medical injection system comprising:
a sensor subassembly including a substrate, and a pressure sensor mounted on the substrate;
a protective apparatus extending over the pressure sensor, the protective apparatus comprising:
a plate including a first side, a second side, opposite the first side, and an opening extending from the first side to the second side, the second side of the plate defining a cavity with the pressure sensor;
a sleeve extending around an outer perimeter surface of the plate and of the pressure sensor; and
a flexible diaphragm extending over the first side of the plate and defining a compressible cavity with the first side of the plate, the compressible cavity being in fluid communication with the cavity formed between the second side of the plate and the coupled pressure sensor, via the opening of the plate, the diaphragm being formed from a rubber material, and the diaphragm including a central zone, an undulating peripheral zone, and a perimeter edge, the perimeter edge being attached to the sleeve between the sleeve and the outer perimeter surface of the plate, and the peripheral zone including a series of annular corrugations and a series of spoke-like corrugations, each spoke-like corrugation radiating from the central zone to the perimeter edge and intersecting each annular corrugation; and
a cap coupled to the sleeve of the protective apparatus, the cap comprising an inner surface that defines a flow chamber, at least one inlet port for flow into the flow chamber, and an outlet port for flow out from the flow chamber, the flow chamber being located on an opposite side of the diaphragm of the protective apparatus from the compressible cavity.

13. The assembly of claim 12, wherein:
the pressure sensor of the sensor subassembly comprises a sensing element, an isolation layer overlaying the sensing element, and a cup mounted on the substrate, the cup containing the sensing element and the isolation layer, the cup having an opening that faces away from the substrate and exposes a surface of the isolation layer;
the second side of the plate of the protective apparatus defines the cavity with the exposed surface of the isolation layer of the pressure sensor, a maximum depth of the exposed surface of the isolation layer, relative to the second side of the plate, being no greater than approximately 0.035 inch; and
the sleeve is bonded to the cup of the pressure sensor.

14. The assembly of claim 12, wherein the at least one inlet port of the cap comprises a pair of inlet ports.

15. The assembly of claim 12, wherein the first side of the plate of the protective apparatus has an undulating contour formed therein, the undulating contour generally aligned with, and simulating the series of annular corrugations of the undulating peripheral zone of the diaphragm.

16. The assembly of claim 12, wherein a compressible fluid volume contained within the cavities, on either side of the plate of the protective apparatus, and within the opening of the plate is no greater than approximately six cubic millimeters.

17. The assembly of claim 12, wherein a ratio of a compressible fluid volume contained within the compressible cavity, on the first side of the plate of the protective apparatus, to a compressible fluid volume contained within the cavity, on the second side of the plate, is between approximately one and approximately three.

18. The assembly of claim 12, wherein a maximum diameter of the plate of the protective apparatus, defined at the outer perimeter surface thereof, is between approximately 2.5 mm (0.1 inch) and approximately 3 mm (0.12 inch).

19. The assembly of claim 12, wherein the outer perimeter surface of the plate of the protective apparatus is tapered such that a maximum diameter of the plate is located on the second side of the plate.

20. The assembly of claim 12, wherein a diameter of the opening of the plate of the protective apparatus is approximately 0.25 mm (0.01 inch).

21. The assembly of claim 12, wherein a nominal thickness of the central zone of the diaphragm of the protective apparatus is greater than a diameter of the opening of the plate of the protective apparatus.

22. The assembly of claim 12, wherein the central zone of the diaphragm of the protective apparatus has a stiffness greater than the peripheral zone of the diaphragm, the central zone being aligned over the opening of the plate of the protective apparatus.

23. The assembly of claim 12, wherein the diaphragm of the protective apparatus is formed by injection molding, and the central zone of the diaphragm comprises a mold gate vestige.

24. The assembly of claim 12, wherein a nominal thickness of the undulating peripheral zone of the diaphragm of the protective apparatus is between approximately 0.01 inch and approximately 0.012 inch.

25. A manifold connector for use in a medical injection system, the manifold connector comprising an injection channel and an auxiliary channel in fluid communication therewith; the injection channel of the manifold connector comprising:

a wall defining a lumen of the channel and having an aperture formed therethrough, the aperture having a perimeter surface configured to retain a blood pressure-monitoring pressure sensor therein; and a protective apparatus mounted within the aperture of the wall, the protective apparatus comprising:

a plate including a first side facing toward the lumen of the channel, a second side, opposite the first side, and an opening extending from the first side to the second, the second side of the plate defining a cavity with the pressure sensor when the pressure sensor is retained in the aperture; and a flexible diaphragm extending between the first side of the plate and the lumen of the channel, the diaphragm defining a compressible cavity with the first side of the plate, the compressible cavity being in fluid communication with the cavity formed between the second side of the plate and the coupled pressure sensor, via the opening of the plate, the diaphragm being formed from a rubber material, and the diaphragm including a central zone, an undulating peripheral zone, and a perimeter edge, the peripheral zone including a series of annular corrugations and a series of spoke-like corrugations, each spoke-like corrugation radiating from the central zone to the perimeter edge and intersecting each annular corrugation; and wherein the perimeter edge of the diaphragm is captured between an outer perimeter surface of the plate and the perimeter surface of the aperture formed through the wall of the channel, and a side of the diaphragm, opposite the compressible cavity, is in fluid communication with the lumen of the channel.

26. The manifold connector of claim 25, wherein:

the auxiliary channel extends between a proximal end of the auxiliary channel and a distal end of the auxiliary channel for insertion of an elongate medical device therethrough, from the proximal end, the proximal end having an adjustable sealing member formed therein, and the distal end being configured for connection to a delivery catheter; and the injection channel is offset from the auxiliary channel such that passage of the elongate medical device through the auxiliary channel, from the proximal end thereof, will not impinge upon the protective apparatus.

27. The manifold connector of claim 25, further comprising a sensor subassembly, the sensor subassembly including a substrate and the pressure sensor mounted on the substrate and retained in the aperture of the wall of the injection channel; and wherein the retained pressure sensor extends within the aperture of the wall of the injection channel to define the cavity with the second side of the plate of the protective apparatus.

28. The manifold connector of claim 27, wherein:

the pressure sensor comprises a sensing element, an isolation layer overlaying the sensing element, and a cup mounted on the substrate, the cup containing the sensing element and the isolation layer, the cup having an opening that faces away from the substrate and exposes a surface of the isolation layer;

the second side of the plate of the protective apparatus defines the cavity with the exposed surface of the isolation layer of the pressure sensor, a maximum depth of the exposed surface, relative to the second side of the plate, being no greater than approximately 0.035 inch; and the perimeter surface of the aperture of the wall of the injection channel extends around the outer perimeter surface of the cup of the pressure sensor.

29. The assembly of claim 25, wherein the first side of the plate of the protective apparatus has an undulating contour formed therein, the undulating contour generally aligned with, and simulating the series of annular corrugations of the undulating peripheral zone of the diaphragm.

30. The assembly of claim 25, wherein a compressible fluid volume contained within the cavities, on either side of the plate of the protective apparatus, and within the opening of the plate is no greater than approximately six cubic millimeters.

31. The assembly of claim 25, wherein a ratio of a compressible fluid volume contained within the compressible cavity, on the first side of the plate of the protective apparatus, to a compressible fluid volume contained within the cavity, on the second side of the plate, is between approximately one and approximately three.

32. The assembly of claim 25, wherein a diameter of the plate of the protective apparatus, defined at the outer perimeter surface thereof, is between approximately 2.5 mm (0.1 inch) and approximately 3 mm (0.12 inch).

33. The assembly of claim 25, wherein a diameter of the opening of the plate of the protective apparatus is approximately 0.25 mm (0.01 inch).

34. The assembly of claim 25, wherein a nominal thickness of the central zone of the diaphragm of the protective apparatus is greater than a diameter of the opening of the plate of the protective apparatus.

35. The assembly of claim 25, wherein the central zone of the diaphragm of the protective apparatus has a stiffness greater than the peripheral zone of the diaphragm, the central zone being aligned over the opening of the plate of the protective apparatus.

36. The assembly of claim 25, wherein the diaphragm of the protective apparatus is formed by injection molding, and the central zone of the diaphragm comprises a mold gate vestige.

37. The assembly of claim 25, wherein a nominal thickness of the undulating peripheral zone of the diaphragm of the protective apparatus is between approximately 0.01 inch and approximately 0.012 inch.

38. A fluid circuit line comprising:

a wall defining a lumen of the line and having an aperture formed therethrough, the aperture having a perimeter surface configured to retain a pressure sensor therein; and a protective apparatus mounted within the aperture of the wall, the protective apparatus comprising:

a plate including a first side facing toward the lumen, a second side, opposite the first side, and an opening extending from the first side to the second, the second side of the plate defining a cavity with the pressure sensor, when the pressure sensor is retained in the aperture; and a flexible diaphragm extending between the first side of the plate and the lumen, the diaphragm defining a compressible cavity with the first side of the plate, the compressible cavity being in fluid communication with the cavity formed between the second side of the plate and the coupled pressure sensor, via the opening of the plate, the diaphragm being formed from a rubber material, and the diaphragm including a central zone, an undulating peripheral zone, and a perimeter edge, the peripheral zone including a series of annular corrugations and a series of spoke-like corrugations, each spoke-like corrugation radiating from the central zone to the perimeter edge and intersecting each annular corrugation; and wherein the perimeter edge of the diaphragm is captured between an outer perimeter surface of the plate and the perimeter surface of the aperture, and a side of the diaphragm, opposite the compressible cavity, is in fluid communication with the lumen.

39. A flow circuit assembly comprising:

a sensor subassembly including a substrate, and a pressure sensor mounted on the substrate;

a protective apparatus extending over the pressure sensor, the protective apparatus comprising:

a plate including a first side, a second side, opposite the first side, and an opening extending from the first side to the second side, the second side of the plate defining a cavity with the pressure sensor;

a sleeve extending around an outer perimeter surface of the plate and of the pressure sensor; and a flexible diaphragm extending over the first side of the plate and defining a compressible cavity with the first side of the plate, the compressible cavity being in fluid communication with the cavity formed between the second side of the plate and the coupled pressure sensor, via the opening of the plate, the diaphragm being formed from a rubber material, and the diaphragm including a central zone, an undulating peripheral zone, and a perimeter edge, the perimeter edge being attached to the sleeve between the sleeve and the outer perimeter surface of the plate, and the peripheral zone including a series of annular corrugations and a series of spoke-like corrugations, each spoke-like corrugation radiating from the central zone to the perimeter edge and intersecting each annular corrugation the central zone having a stiffness greater than the peripheral zone, the central zone being aligned over the opening of the plate; and a cap coupled to the sleeve of the protective apparatus, the cap comprising an inner surface that defines a flow chamber, a pair of inlet ports for flow into the flow chamber, and an outlet port for flow out from the flow chamber, the flow chamber being located on an opposite side of the diaphragm of the protective apparatus from the compressible cavity.

* * * * *